(12) United States Patent
Li et al.

(10) Patent No.: US 7,964,219 B2
(45) Date of Patent: Jun. 21, 2011

(54) PHARMACEUTICAL COMPOSITIONS FOR CONTROLLED RELEASE DELIVERY OF BIOLOGICALLY ACTIVE COMPOUNDS

(75) Inventors: Yuhua Li, Newark, DE (US); Benjamin Chien, Newark, DE (US)

(73) Assignee: QPS, LLC, Newark, DE (US)

(*) Notice: Subject to any disclaimer, the term of this patent is extended or adjusted under 35 U.S.C. 154(b) by 1547 days.

(21) Appl. No.: 11/201,932

(22) Filed: Aug. 11, 2005

(65) Prior Publication Data

US 2006/0034923 A1 Feb. 16, 2006

Related U.S. Application Data

(60) Provisional application No. 60/600,907, filed on Aug. 12, 2004.

(51) Int. Cl.
*A61K 31/663* (2006.01)
(52) U.S. Cl. .................. 424/501; 424/468; 514/102
(58) Field of Classification Search .................. None
See application file for complete search history.

(56) References Cited

U.S. PATENT DOCUMENTS

| | | | |
|---|---|---|---|
| 4,578,384 A * | 3/1986 | Hollinger | 514/8 |
| 4,675,189 A | 6/1987 | Kent et al. | |
| 4,728,721 A | 3/1988 | Yamamoto et al. | |
| 4,767,628 A | 8/1988 | Hutchinson | |
| 4,938,763 A | 7/1990 | Dunn et al. | |
| 5,059,591 A * | 10/1991 | Janoff et al. | 514/31 |
| 5,077,049 A | 12/1991 | Dunn et al. | |
| 5,225,205 A | 7/1993 | Orsolini | |
| 5,278,201 A | 1/1994 | Dunn et al. | |
| 5,278,202 A | 1/1994 | Dunn et al. | |
| 5,410,016 A | 4/1995 | Hubbell et al. | |
| 5,480,656 A | 1/1996 | Okada et al. | |
| 5,501,863 A | 3/1996 | Rössling et al. | |
| 5,529,914 A | 6/1996 | Hubbell et al. | |
| 5,538,739 A | 7/1996 | Bodmer et al. | |
| 5,595,760 A * | 1/1997 | Cherif-Cheikh | 424/464 |
| 5,614,510 A * | 3/1997 | Persson | 514/103 |
| 5,654,010 A | 8/1997 | Johnson et al. | |
| 5,698,213 A | 12/1997 | Jamiolkowski et al. | |
| 5,739,176 A | 4/1998 | Dunn et al. | |
| 6,312,679 B1 | 11/2001 | Tomalia et al. | |
| 6,410,044 B1 | 6/2002 | Chudzik et al. | |
| 6,528,080 B2 | 3/2003 | Dunn et al. | |
| 6,589,548 B1 * | 7/2003 | Oh et al. | 424/426 |
| 6,592,899 B2 * | 7/2003 | Fowers et al. | 424/486 |
| 2004/0228833 A1 | 11/2004 | Costantino et al. | |

FOREIGN PATENT DOCUMENTS

| | | | |
|---|---|---|---|
| EP | 0058481 | | 8/1982 |
| JP | 04026630 | | 1/1992 |
| WO | WO 93/16687 | | 9/1993 |
| WO | WO 93/17668 | | 9/1993 |
| WO | WO/96/21440 | * | 7/1996 |
| WO | WO/02/10177 | * | 2/2002 |
| WO | WO/2004/045633 | * | 6/2004 |

OTHER PUBLICATIONS

Jeong, et al, New Biodegradable Polymers for Injectable Drug Delivery Systems, 1999, Journal of Controlled Release, Elsevier, vol. 62, pp. 109-114.*
Evidentiary reference taken from http://www.sigmaaldrich.com/catalog/search/ProductDetail/SIGMA/P9763.*
Journal of Molecular Biology, 1H-NMR Assignment and Solution Structure of Human Acidic Fibroblast Growth Factor Activated by Inositol Hexaphosphate, by Pineda-Lucena et al, vol. 242, issue 1, pp. 81-98 (abstract only).*
Myo-inositol product information taken from http://chemicalland21.com/lifescience/foco/INOSITIOL.htm.*
Lin et al "Accelerated Degradation of Poly(∈-caprolactone) by Organic Amines," Pharmaceutical Research, vol. 11, No. 7, 1994.*
Jeong et al "New biodegradable polymers for injectable drug delivery Systems," Journal of Controlled Release 62 (1999) 109-114.*
Lin et al "Accelerated Degradation of Poly((-caprolactone) by Organic Amines," Pharmaceutical Research, vol. 11, No. 7, 1994.*
A. Lucke et al., Peptide Acylation by Poly(α-Hydroxy Esters), *Pharm. Research*, vol. 19, No. 2, Feb. 2002.
W. Lin et al., Accelerated Degradation of Poly(∈-caprolactone) by Organic Amines, *Pharm. Research*, vol. 11, No. 7, (1994).
M. Krishnan et al., FTIR-ATR spectroscopy for monitoring plyanhydride/anhydride-amine reactions, *J. Controlled Release* 69 (2000) p. 273-281.
D. Hee Na et al., Monitoring of peptide acylation inside degrading PLGA microspheres by capillary electrophoresis and MALDI-TOF mass spectrometry, *J. Controlled Release* 92 (2003) p. 291-299.
A. Lucke et al., Peptide Acylation by Poly (α-Hydroxy Esters), *Pharm. Research* vol. 19 No. 2, Feb. 2002.
V. Sinha et al., Biodegradable microspheres for protein delivery, *J. Controlled Release*, 90 (2003) p. 261-280.
S. Schwendeman, Recent Advances in the Stabilization of Proteins Encapsulated in Injectable PLGA Delivery Systems, *Critical Reviews in Therapeutic Drug Carrier Systems*, 19(1): 73-98 (2002).
A. Domb et al., Chemical Interactions Between Drugs Containing Reactive Amines with Hydrolyzable Insoluble Biopolymers in Aqueous Solutions, *Pharm. Research* vol. 11, No. 6 (1994).
D. Birnbaum et al., Molecular weight distribution changes during degradation and release of PLGA nanoparticles containing epirubicin HCI, *J. Biomater. Sci. Polymer Edn.*, vol. 14 No. 1, pp. 87-102 (2003).
Lin et al., Accelerated degradation of poly(epsilon-caprolactone by organic amines, *Pharm. Res.* 1994.

* cited by examiner

Primary Examiner — Yvonne L Eyler
Assistant Examiner — Suzanne Ziska
(74) Attorney, Agent, or Firm — Cohen Pontani Lieberman & Pavane LLP

(57) ABSTRACT

The present invention provides compositions and methods for the controlled release delivery of one or more biologically active compounds to a subject. Specifically, the invention provides for a pharmaceutical composition for the controlled release delivery of biologically active compounds to a subject comprising: a) a complex of a biologically active compound having at least one basic functional group and a polyanion derived from hexahydroxycyclohexane having at least two negatively charged functional groups; and b) a pharmaceutically acceptable carrier comprising a biodegradable, water-insoluble polymer. By complexing a biologically active compound with a polyanion, the tight, stable complex may be incorporated into a long-acting dosage system having a more desired drug release curve over time than that is found in the prior art. The invention also provides the methods of making such compositions and the methods of use thereof.

19 Claims, No Drawings

PHARMACEUTICAL COMPOSITIONS FOR CONTROLLED RELEASE DELIVERY OF BIOLOGICALLY ACTIVE COMPOUNDS

This application claims priority from U.S. Provisional Patent Application Ser. No. 60/600,907 which was filed on Aug. 12, 2004.

FIELD OF THE INVENTION

This invention relates to the field of controlled release delivery of biologically active compounds and to compositions and methods useful for the controlled release delivery of biologically active compounds containing at least one basic group.

BACKGROUND OF THE INVENTION

The ability to deliver biologically active compounds in a controlled manner over a period of time is an ongoing challenge. The controlled release delivery of biologically active compounds can improve the bioavailability by protecting them against degradation in vivo and concomitantly replace multiple injections or continuous infusions which are necessary due to the short half-life of these biologically active compounds. Reduced frequency for administration could improve patient compliance. Biodegradable polymers have been used for more than three decades as drug carriers in implantable devices [Langer, R. and Chasin, M. (Eds) *Polymers as Drug Delivery Systems*, Marcel Dekker, New York, N.Y., 1990]. The advantage of using biodegradable polymers as sustained delivery carriers for biologically active compounds is that they do not require removal after delivering their dose because they are hydrolyzed to soluble non-toxic oligomers or monomers. The biodegradation rate depends on the physicochemical properties of the polymers, including crystallinity, hydrophobicity, chemical structure, molecular weight and molecular weight distribution. Theoretically, these properties can be designed or tailored to develop drug delivery systems in a controlled release manner and desired duration of treatment.

Various biologically active compounds have been described in the prior art in combination with biodegradable polymers to achieve extended release by using appropriate polymers under physiological conditions. The biologically active compound in compositions of the prior art can be in the form of an uncharged molecule, molecular complex, salt, ether, ester, or amide [U.S. Pat. Nos. 6,528,080, 5,739,176, 5,077,049 and 4,938,763]. Specific examples of salts used in injectable or implantable compositions include acetate, chloride, citrate, maleate, phosphate, succinate, sulfate, tartrate, etc. However, the success of such formulations is limited to a few biologically active compounds which are stable and have a wide therapeutic blood concentration range, e.g., leuprolide, gosorelin and rhGH. If a biologically active compound contains reactive functional groups and has a narrow therapeutic blood concentration window, the successful development of controlled release delivery systems for such a biologically active compound has been very challenging. This is primarily due to the instability of the biologically active compounds in the delivery systems and uncontrolled release pattern of the biologically active compounds from the delivery systems, e.g., burst effect at the beginning, in the middle, and at the end of the release. Some biologically active compounds contain basic groups (including primary, secondary, and tertiary amines) may pose serious obstacles for successful development of controlled release delivery systems using biodegradable polymers. The compounds may alter (or catalyze) the hydrolysis process of the polymer carrier in an uncontrolled manner and/or react with the polymers or their degradation products to form undesired amide drug derivatives. The formation of these derivatives not only decreases the dose actually delivered, but also may causes unexpected side effect. The interaction/reaction between biologically active compound and polymer carriers may occur either 1) during formulation when the biologically active compounds are incorporated in the polymer carrier, such as microencapsulation, injection molding, extrusion molding, mixing with polymer solutions in organic solvent, etc.; 2) during storage and 3) during the process of biodegradation and the release of biologically active compounds in vivo.

The interaction/reaction between biologically active compounds contain basic functional groups, i.e., amines, and polymers were reported during the microparticle formation process using solvent evaporation/extraction methods where the biologically active compound and polymer were dissolved/dispersed in organic solvents [Krishnan M. and Flanagan D R., *J Control Release.* 2000 Nov. 3; 69(2):273-81]. Significant amount of amide moieties were formed. It was clearly shown that commonly used solvents for fabrication of biodegradable polymer drug delivery systems could permit rapid reaction between biologically active compound and polymer. In another study, the accelerated degradation of polymers by organic amines was reported [Lin W J, Flanagan D R, Linhardt R J. *Pharm Res.* 1994 July; 11(7):1030-4.]. It was also reported that the degradation of polymer matrix containing simple drug salts, e.g., epirubicin HCl, was found to hasten the degradation of the polymers and subsequently affect the release behavior from these particles [Birnbaum D T, Brannon-Peppas L. *Molecular weight distribution changes during degradation and release of PLGA nanoparticles containing epirubicin HCl. J Biomater Sci Polym Ed.* 2003; 14(1):87-102]. Domb et al reported the drugs containing reactive amines and their salts in the in vitro aqueous degradation media also expedites the degradation of biodegradable polymers [Domb A J, Turovsky L, Nudelman R., *Pharm Res.* 1994 June; 11(6):865-8]. Both of the reaction and catalyzed degradation are undesirable for the controlled release delivery of biologically active compounds for a prolonged time period.

When biodegradable polymers such as polylactic acid, polyglycolic acid, polyhydroxybutyric acid, polyortho-esters, polyacetals and the like are used as drug delivery systems, the biodegradation of polymers (such as polylactide and polylactide-co-glycolide for example) leads to water-uptake and generation of aqueous channels or pores from which biologically active compounds can leak out (or diffuse out) if they become water soluble. In addition, the accumulation of polymer degradation products lowers pH within the degrading polymer matrices and local pH values between 1.5 and 4.7 have been recently reported (Na D H, Youn Y S, Lee S D, Son M O, Kim W A, DeLuca P P, Lee K C. *Monitoring of peptide acylation inside degrading PLGA microspheres by capillary electrophoresis and MALDI-TOF mass spectrometry. J Control Release.* 2003 Oct. 30; 92(3):291-9; and references cited therein). The acidic microenvironment inside the polymer matrices can induce several undesired chemical degradation reactions, especially for the biologically active compounds containing reactive amine groups, such as peptides and proteins.

More examples with respect to the instability or reaction/interaction of biologically active compounds and polymers during formulation, storage, and in vivo release in the prior art have been reviewed in the literature, [Schwendeman S P., *Recent advances in the stabilization of proteins encapsulated*

*in injectable PLGA delivery systems. Crit Rev Ther Drug Carrier Syst.* 2002; 19(1):73-98; Sinha V R, Trehan A., *Biodegradable microspheres for protein delivery. J Control Release.* 2003 Jul. 31; 90(3):261-80], which are all incorporated herein by reference.

Some organic acids, such as acetic acid, citric acid, benzoic acid, succinic acid, tartaric acid, heparin, ascorbic acid and their non-toxic salts, have been described in the prior art and used in various controlled release biodegradable systems as polymer degradation enhancers. (PCT-patent application WO93/17668 (page 14, lines 4-13) and U.S. Pat. No. 4,675,189) (Column 11, lines 5-19). Thus, such acid additives are not expected to stabilize the polymers.

Various other approaches have been investigated to achieve successful controlled release delivery of biologically active compounds containing reactive basic groups. However, despite tremendous research efforts, there are only a few products for controlled release delivery of biologically active compounds commercially available so far [see e.g., U.S. Pat. No. 4,728,721 (Leuprolide, Lupron Depot); U.S. Pat. No. 4,938,763 (Leuprolide, Eligard); U.S. Pat. No. 5,225,205 (Triptorelin Pamoate, Trelstar); U.S. Pat. No. 4,767,628 (Goserelin Acetate, Zoladex); U.S. Pat. No. 5,538,739 (Octreotide, SANDOSTATIN LAR); U.S. Pat. No. 5,654,010 (recombinant human growth hormone, Nutropin Depot); U.S. Pat. Nos. 4,675,189; 5,480,656; 4,728,721].

Clearly, there is a need to develop novel and suitable delivery system which stabilizes the biologically active compounds, controls the degradation of polymers, limits the burst effect, and maintains drug release within therapeutic limits for the duration of the treatment. Thus, it is an object of this invention to address the above-enumerated deficiencies in the prior art and provide a pharmaceutical composition for controlled release delivery of biologically active compounds to a subject comprising:
  a) a complex of a biologically active compound having at least one basic functional group and a polyanion derived from hexahydroxycyclohexane having at least two negatively charged functional groups; and
  b) a pharmaceutically acceptable carrier comprising a biodegradable, water-insoluble polymer.

The instant invention also provides methods for producing such controlled release pharmaceutical compositions and methods of use thereof.

SUMMARY OF THE INVENTION

The present invention provides compositions and methods for the controlled release delivery of one or more biologically active compounds to a subject. Specifically, a pharmaceutical composition for controlled release delivery of biologically active compounds to a subject comprising: a) a complex of a biologically active compound having at least one basic functional group and a polyanion derived from hexahydroxycyclohexane having at least two negatively charged functional groups; and b) a pharmaceutically acceptable carrier comprising a biodegradable, water-insoluble polymer. By complexing a biologically active compound with a polyanion, the tight, stable complex may be incorporated into a long-acting dosage system having a low initial burst release and a more desired drug release curve over time than that is found in much of the prior art.

It is surprisingly found that the polyanions of the invention may reduce or prevent the interaction/reaction between biologically active compounds containing basic groups and polymers or their degradation products by forming stable complexes. The complexes may have low solubility in water or biological fluid. Preferably the complexes also have low solubility in the solvents used to prepare the dosage form. These properties can not only stabilize the biologically active compound and slow the degradation of polymer during the formulation process, but also during release by reducing or preventing the interaction/reaction between the biologically active compound and the polymer and/or its degradation products. More importantly, these properties may result in the delivery of biologically active compounds from biodegradable polymer carriers with a highly desirable release profile. It can permit continuous delivery of a biologically active compound to a subject for prolonged periods of time, e.g., from weeks to months to benefit the subject.

It is therefore an object of this invention to provide a pharmaceutical composition for controlled release delivery of biologically active compounds to a subject comprising: a) a complex of a biologically active compound having at least one basic functional group and a polyanion derived from hexahydroxycyclohexane having at least two negatively charged functional groups; and b) a pharmaceutically acceptable carrier comprising a biodegradable, water-insoluble polymer.

It is a further object of the present invention to provide a group of biologically active compounds containing at least one basic functional group that could benefit from the sustained controlled release delivery systems.

It is a further object of the present invention to provide a group of polyanions that can form stable complex with biologically active compounds.

It is a further object of the present invention to provide a process for making the complexes between a biologically active compound and a polyanion of the invention.

It is a further object of the present invention to provide a complex which may reduce or prevent the undesired degradation of polymers by the biologically active compound not only during the formulation and storage, but also during the degradation of polymer and drug release in vivo.

It is a further object of the present invention to provide a complex which may stabilize the biologically active compound not only during formulation and storage, but also during the degradation of polymer and drug release in vivo.

It is a further object of the present invention to provide a pharmaceutically acceptable carrier comprising biodegradable water insoluble polymers having dispersed therein the biologically active compound/polyanion complex that exhibits sustained release of the biologically active compound.

It is a further object of the present invention to provide a pharmaceutically acceptable composition having incorporated therein the biologically active compound/polyanion complex that can release the biologically active compound which has retained their biological activities.

It is a further object of the present invention to provide a pharmaceutically acceptable composition for use in medical applications, such as drug delivery, vaccination, gene therapy, etc.

It is a further object of the present invention to provide a pharmaceutically acceptable composition suitable for oral or parenteral administrations; mucosal administration; ophthalmic administration; subcutaneous, intraarticular, or intramuscular injection; administrations by inhalation; and topical administrations.

These and other objects of the present invention will become apparent after reading the following detailed description of the disclosed embodiments.

DETAILED DESCRIPTION OF THE INVENTION

The present invention relates to pharmaceutical compositions for the controlled release delivery of biologically active compounds to a subject comprising: a) a complex of a biologically active compound having at least one basic functional group and a polyanion derived from hexahydroxycyclohexane having at least two negatively charged functional groups; and b) a pharmaceutically acceptable carrier comprising a biodegradable, water-insoluble polymer, and methods of making and using such compositions. The compositions of the invention can be prepared in any conventional pharmaceutical administration forms by the method known in the art. Non-limiting examples of the compositions of the invention are solutions, suspensions, dispersions, emulsions, drops, aerosols, creams, semisolids, pastes, capsules, tablets, solid implants, or microparticles. The advantages of the pharmaceutical compositions of the invention include low initial burst and stable controlled release of biologically active compounds in vivo. It can permit continuous delivery of a biologically active compound to a subject for prolonged periods of time, e.g., from days to months.

The terms "a", "an" and "one", as used herein, are meant to be interpreted as "one or more" and "at least one."

The term "biologically active compound" is meant to include any materials having diagnostic and/or therapeutic properties including, but not limited to, small molecules, macromolecules, peptides, proteins, or enzymes. Non-limiting examples of therapeutic properties are antimetabolic, antifungal, anti-inflammatory, antitumoral, antiinfectious, antibiotics, nutrient, agonist, and antagonist properties.

More specifically, the biologically active compounds of the invention may be any compounds capable of forming a complex with a polyanion derived from hexahydrocyclohexane, in particular a compound containing an electron donor base group such as a basic nitrogen atom, e.g. an amine, imine or ring nitrogen. The biologically active compounds preferably contain one or more exposed protonatable amine functionalities, particularly preferably a plurality of such groups. Biologically active compounds useful in the preparation of the stable complex of the invention include, but are not limited to, doxorubicin, doxycyclin, diltiazam, cyclobenzaprine, bacitracin, noscapine, erythromycin, polymyxin, vancomycin, nortriptyline, quinidine, ergotamine, benztropine, verapamil, flunarizine, imipramine, gentamycin, kanamycin, neomycin, amoxicillin, amikacin, arbekacin, bambermycins, butirosin, dibekacin, dihydrostreptomycin, fortimicin, isepamicin, micronimicin, netilmicin, paromycin, ribostamycin, rapamycin, sisomicin, streptomycin and tobramycin, amikacin, neomycin, streptomycin and tobramycin, pyrimethamine, naltrexone, lidocaine, prilocalne, mepivacaine, bupivacaine, tetracaine, ropivacaine, oxytocin, vasopressin, adrenocorticotropic hormone (ACTH), epidermal growth factor (EGF), platelet-derived growth factor (PDGF), prolactin, luteinising hormone, luteinizing hormone releasing hormone (LHRH), LHRH agonists, LHRH antagonists, growth hormones (including human, porcine, and bovine), growth hormone releasing factor, insulin, erythropoietin (including all proteins with erythropoietic activity), somatostatin, glucagon, interleukin, interferon-.alpha., interferon-.beta., interferon-.gamma., gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), exenatide, peptide YY (PYY), renin, bradykinin, bacitracins, polymyxins, colistins, tyrocidine, gramicidins, cyclosporins (which includes synthetic analogues and pharmacologically active fragments thereof), enzymes, cytokines, antibodies, vaccines, antibiotics, antibodies, glycoproteins, follicle stimulating hormone, kyotorphin, taftsin, thymopoietin, thymosin, thymostimulin, thymic humoral factor, serum thymic factor, colony stimulating factors, motilin, bombesin, dinorphin, neurotensin, cerulein, urokinase, kallikrein, substance P analogues and antagonists, angiotensin II, blood coagulation factor VII and IX, lysozyme, gramicidines, melanocyte stimulating hormone, thyroid hormone releasing hormone, thyroid stimulating hormone, pancreozymin, cholecystokinin, human placental lactogen, human chorionic gonadotrophin, protein synthesis stimulating peptide, gastric inhibitory peptide, vasoactive intestinal peptide, platelet derived growth factor, and synthetic analogues and modifications and pharmacologically-active fragments thereof.

The term "polyanion", as defined herein, is meant to include any molecules containing at least two or more negatively charged functional groups. Polyanions of the invention are derived from hexahydroxycyclohexane by esterifying with phosphate or sulfate groups capable of forming stable complexes with the biologically active compounds. Myo-inositol is one of nine known cis-trans isomers of hexahydroxycyclohexane, a 6-carbon ring structure found in abundance in plants and animals. For example, inositol hexaphosphate (InP6, phytic acid) is a natural dietary ingredient and constitutes 0.4-6.4% (w/w) of most cereals, legumes, nuts, oil seeds and soybean. An expanding body of evidence indicates that many, if not all, mammalian cells contain inositol polyphosphates with 5 or more phosphate groups. For example, InP6 is found in most mammalian cells, where it may assist in regulating a variety of important cellular functions. InP6 has also been shown to function as an antioxidant by chelating divalent cations such as copper and iron, preventing the generation of reactive oxygen species responsible for cell injury and carcinogenesis. Some other examples of inositol polyanion include, but not limited to, lower inositol phosphates, (i.e., inositol pentaphosphate, inositol tetraphosphate, inositol triphosphate, inositol diphosphate), and other polyphosphorylated organic compounds, inositol hexasulphate (InS6) and lower inositol sulfates. The polyanions can be either in acid or in salt forms.

The polyanions of at least two or more negatively charged groups are especially preferred, in particular, the inositol hexaphosphate (InP6, phytic acid), and inositol hexasulphate (InS6).

The term "stable complex" is meant to refer to a physically and chemically stable complex that forms upon appropriate combining of a biologically active compound and polyanion under conditions such that a stable complex is formed, e.g., aqueous solutions of the biologically active compound and polyanion are mixed until the complex forms. The complex may be in the form of a solid (e.g., a paste, granules, a powder or a lyophilizate) or the powdered form of the complex can be pulverized finely enough to be homogeneously dispersed in biodegradable polymer carriers. This complex typically takes the form of a precipitate that is produced upon combining aqueous preparations of the biologically active compound and polyanion. Optionally, one or more pharmaceutically acceptable excipients may be incorporated into the complex. Such excipients may function as stabilizers for the biologically active compound or its complex. Non-limiting examples include sodium bisulfite, p-aminobenzoic acid, thiourea, glycine, methionine, mannitol, sucrose, polyethylene glycol (PEG), and the like.

By way of example, a soluble antibiotics (e.g. doxorubicin) may be dissolved in water and a solution of InP6 may be added thereto. The drug:InP6 complex precipitates out. The precipitates can be washed and then separated by centrifugation or filtration. The separated complex was dried under vacuum.

As a further example, to a solution of a local anesthetic (e.g. tetracaine hydrochloride) there may be added an aqueous solution of InP6. The drug:InP6 complex precipitates out.

As a further example, to a solution of a peptide (e.g. glycagon like peptide 1 (GLP-1)) there may be added an aqueous solution of InP6. The peptide:InP6 complex precipitates out. The precipitates can be washed and then separated by centrifugation or filtration. The separated complex was dried under vacuum.

As a further example, to a solution of an enzyme (e.g. lysozyme) there may be added an aqueous solution of InP6. The enzyme:InP6 complex precipitates out. The precipitates can be washed and then separated by centrifugation or filtration. The separated complex was dried under vacuum.

The stable complex between a biologically active compound and polyanion of the invention can be incorporated into a pharmaceutically acceptable carrier comprising biodegradable water-insoluble polymers, optionally with some excipients. The term "biodegradable water-insoluble polymer" is meant to include any biocompatible and/or biodegradable synthetic and natural polymers that can be used in vivo. The "biodegradable water-insoluble polymer" is also meant to include the polymers that are insoluble or become insoluble in water or biological fluid at 37° C. The polymers may be purified, optionally, to remove monomers and oligomers using techniques known in the art (e.g, U.S. Pat. No. 4,728,721). Some non-limiting examples of the polymers are polylactides, polyglycolides, poly(lactide-co-glycolide)s, polycaprolactones, polydioxanones, polycarbonates, polyhydroxybutyrates, polyalkylene oxalates, polyanhydrides, polyamides, polyesteramides, polyurethanes, polyacetals, polyorthocarbonates, polyphosphazenes, polyhydroxyvalerates, polyalkylene succinates, and polyorthoesters, and copolymers, block copolymers, branched copolymers, terpolymers and combinations and mixtures thereof.

Further, the biodegradable water-insoluble polymer can include end capped, end uncapped, or a blend of end capped, end uncapped polymers. An end capped polymer is generally defined as having capped carboxyl end groups. An uncapped polymer is as classically defined in the art, specifically having free carboxyl end groups.

Suitable molecular weights for polymers may be determined by a person of ordinary skill in the art. Factors that may be considered when determining molecular weights include desired polymer degradation rate, mechanical strength, and rate of dissolution of polymer in solvent. Typically, a suitable range of molecular weights of polymers is of about 2,000 Daltons to about 150,000 Daltons with a polydispersity of from 1.1 to 2.8, depending upon which polymer is selected for use, among other factors.

As used herein, the term of "pharmaceutically acceptable carrier" is intended to include any carriers with environment responsive properties (e.g., thermosensitive, pH sensitive, electrical sensitive, etc.), injectable solutions or suspensions, particles, films, pellets, cylinders, discs, microcapsules, microspheres, nanospheres, microparticles, wafers, micelles, liposomes, and other known polymeric configurations used for drug delivery.

Methods for forming various pharmaceutically acceptable polymer carriers are well known in the art. For examples, various methods and materials are described in U.S. Pat. Nos. 6,410,044; 5,698,213; 6,312,679; 5,410,016; 5.529,914; 5,501,863; and PCT Publication No. WO 93/16687; U.S. Pat. Nos. 4,938,763; 5,278,201; 5,278,202; EP 0,058,481; which are all incorporated herein by reference.

According to the invention, compositions can be produced when biologically active compound/polyanion complex are dispersed in polymeric matrix to form solid implants, which can be injected or implanted to a subject. These implants can be prepared from the biologically active compound/polyanion complex of the invention, optionally containing pharmaceutically acceptable excipients, using conventional polymer melt-processing techniques, such as, but not limited to, extrusion, compression and injection molding, wherein elevated temperatures (preferably less than 100° C.) are used to melt the polymer matrix in the preparation of the implant. Preparations of such implants can be carried out under aseptic conditions, or alternatively by terminal sterilization by irradiation, using but not limited to, Gamma irradiation or electron beam sterilization.

According to one embodiment of the present invention, homogeneous mixture of biologically active compound/polyanion complexes and polymers can be prepared by dry-mixing in any appropriate apparatus, for example in a ball mill, and at room temperature or even at a lower temperature, for example <10° C. The proportion of the powdered components can vary within a broad range, for example from 0.1 to 30% in weight for the biologically active compound, depending upon the therapeutic effects required. Homogeneous mixture of biologically active compound/polyanion complexes and polymers can also be prepared by dispersing the complexes in polymer solution in an organic solvent, followed by the removal of the organic solvent by evaporation or lyophilization. The resulting solid can be pulverized to fine powders.

According to the invention, once a given mixture is well homogenized, it can be molded using the techniques known in the art. For example, it can be progressively compressed with progressive heating before being molded. The compression ratio may vary depending on numerous factors, such as the geometry of the apparatus or the grain size of the powdered mixture. The control of the preheating and of the change it undergoes as the mixture progresses is more critical: depending upon the nature of the products to be treated (copolymer, biologically active compound), every endeavor is made to maintain a temperature gradient not exceeding approximately 100° C. The initial temperature to which the powdered mixture is subjected can be 25° C., lower or higher, depending on circumstances.

The molding temperature should be kept as low as possible, preferably, not exceed 100° C., and the upper limit of the temperature is dictated by the nature of the biologically active compound, which should not undergo deterioration. An adequate pressure and an adequate temperature promote the perfect homogenization of the ingredients and, in particular, the uniform distribution of the complex throughout the mass of the copolymer can be readily determined by simple experimentations.

Alternatively, the homogenized powders can be compression molded at room temperature, similar to the preparation of FTIR pellet.

In one embodiment of the invention, a copolymer of D,L-lactide and glycolide with a 50/50 molar ratio of D,L-lactide to glycolide is dissolved in methylene chloride. To this solution, tetracaine phytate is added and dispersed with a high shear mixer. The resulting mixture is placed in a rotating evaporator and the majority of the methylene chloride is removed under vacuum. The resulting thick dispersion is poured onto a glass plate to form a film. The film thus obtained is melted and compression molded to give a film about 0.5 mm thick.

According to the invention, alternatively, the homogenized powders can be melted and compression extruded or injection molded into different shapes of solid implants as known in the art. The actual extrusion can be carried out by means of a nozzle of standard shape and dimensions. The cooling of the extruded product is achieved by any appropriate means, such as cold sterile air or gas or simply through natural loss of heat.

According to the invention, these solid dosage forms, e.g., fiber, rod, film, or wafer, can be reduced to microparticulate forms by comminution or milling. The extruded or molded product described above adequately cooled is then pulverized at low temperature, preferably at a temperature lower than 0° C., or even much lower, for example −20° C. The product thus pulverized may then be subjected to sieving to obtain desired particle size. The preferred particle sizes may range from 1 µm to 500 µm, and these microparticle delivery systems can be suspended in a suitable conventional pharmaceutically acceptable injection vehicle.

According to another aspect of the invention, particularly effective and useful parenteral pharmaceutical formulations of biologically active compounds can also be prepared in the form of solutions or suspensions of a polymer in a pharmaceutically acceptable solvent containing dispersed or solubilized drug/polyanion complex. By complexation with a polyanion, the reactive groups in biologically active compound are not available to interact with polymer in solution. Thus, the stability of biologically active compound in the compositions of the present invention was improved by complexing with polyanions of the invention.

Thus, according to the present invention, however, there is provided a pharmaceutical composition comprising a biologically active compound complexed with a polyanion and a polymer, for extended release of the biologically active compound, characterized in that the composition is in the form of an injectable solution/suspension, comprising:
  (a) a complex of a biologically active compound having at least one basic functional group and a derivative of hexahydroxycyclohexane having at least two negatively charged functional groups; and
  (b) a biodegradable water-insoluble polymer;
  (c) a pharmaceutically acceptable organic solvent which is a solvent for the polymer Suitable biologically active compound and polyanion are those defined above, and particularly preferred polyanions are those containing at least two phosphate or sulfate groups as defined above, more preferably InP6 or InS6.

The molar ratio of biologically active compound to polyanion in the complex will vary from 0.1:1 to 1:0.1 according to the nature of biologically active compound and polyanion, and the period of peptide drug release desired.

Any suitable biodegradable polymer can be employed, provided the polymer is insoluble or become insoluble in aqueous medium or body fluid at 37° C. Suitable biodegradable polymers are those defined above.

The type, molecular weight, and amount of biodegradable polymer present in the compositions can influence the length of time in which the biologically active compound is released from the controlled release implant. The selection of the type, molecular weight, and amount of biodegradable polymer present in the compositions to achieve desired properties of the controlled release implant can be performed by a person with ordinary skills in the art.

Suitable pharmaceutically acceptable organic solvent include, but not limited to, N-methyl-2-pyrrolidone, N,N-dimethylformamide, dimethyl sulfoxide, propylene carbonate, caprolactam, triacetin, benzyl benzoate, benzyl alcohol, ethyl lactate, glyceryl triacetate, esters of citric acid, and polyethylene glycols, alkoxypolyethylene glycols and polyethylene glycol acetates, etc., or any combination thereof.

The criteria for the organic solvents of biodegradable polymers are that they are pharmaceutically acceptable and miscible to dispersible in aqueous medium or body fluid. The suitable organic solvent should be able to diffuse into body fluid so that the liquid composition coagulates or solidifies to form an implant in place. Single and/or mixture of such solvents can be employed, the suitability of such solvents can be determined readily by simple experimentations.

The pharmaceutical compositions of the invention typically contain biologically active compound in a range of 0.1 to 40% w/v. In general, the optimal drug loading is dependent upon the period of release desired and the potency of the biologically active compound. Obviously, for biologically active compound of low potency and longer period of release, higher levels of incorporation may be required.

The viscosity of the solution compositions of the invention is determined by the molecular weight of the polymer and organic solvent used. For example, when poly(lactide-co-glycolide) is used, the solution of polyester in NMP has a lower viscosity than in mPEG350. Typically, when the same solvent is used, the higher the molecular weight and concentration of the polymer, the higher the viscosity. Preferably the concentration of the polymer in solutions is below 70% by weight. More preferably concentration of the polymer in solutions is between 20 to 50% by weight.

Preferably, the complex should have a low solubility in organic solvent used. The reactive groups of the biologically active compound will be bound to the polyanion and thus are not available for interaction/reaction with polymer or solvent. This greatly reduces the risk of unfavorable interaction/reaction with the polymer and its degradation products.

According to one embodiment of the present invention, a simple salt, tetracaine chloride, is mixed with 50/50 poly(DL-lactide-co-glycolide) having a carboxy terminal group solution in NMP. For the in vitro studies, small drops of the mixture (about 100 mg) are added to phosphate buffered saline solution. The receiving fluid is replaced at selected time points with fresh solution, and the removed PBS solution is analyzed for drug concentration using appropriate analytical methods.

According to another embodiment of the present invention, tetracaine phytate is mixed with 50/50 poly(DL-lactide-co-glycolide) having a carboxy terminal group solution in NMP. The drug complex was dispersed uniformly in the polymer solution. For the in vitro studies, small drops of the mixture (about 100 mg) are added to phosphate buffered saline solution. The receiving fluid is replaced at predefined time points with fresh solution, and the removed PBS solution is analyzed for drug concentration using appropriate analytical methods.

According to another embodiment of the present invention, octreotide phytate and octretide acetate were mixed with 50/50 poly(DL-lactide-co-glycolide) having a carboxy terminal group solution in NMP and methoxypolyethylene glycol 350. The drug complex was dispersed uniformly in the polymer solutions. The compositions were kept at room temperature and the stability of octreotide in the composition was monitored by HPLC analysis over time. The complexation of octreotide with phytic acid significantly improved the stability of octreotide in the composition over time.

According to another embodiment of the present invention, octreotide phytate and octretide acetate were mixed with 50/50 poly(DL-lactide-co-glycolide) having a carboxy terminal group solution in NMP and methoxypolyethylene glycol 350. The drug complex was dispersed uniformly in the polymer solutions. The compositions were administered subcutaneously in Sprague-Dawley male rats to form an implant in place. The initial release of octreotide was determined by implant retrieval at predefined time intervals after administration and analysis of the octreotide remaining in the implant. The stability of octreotide during the formulation and release was also evaluated. The complexation of octreotide with phytic acid significantly lowered the initial release of octreotide and improved the stability of octreotide during the release process over time.

The release of biologically active compound from these implants formed in place will follow the same general rules for release of a drug from a monolithic polymeric device. The release of biologically active compound can be affected by the size and shape of the implant, the loading of biologically active compound within the implant, the permeability factors involving the biologically active compound and the particular polymer, and the degradation of the polymer. Depending upon the amount of biologically active compound selected for delivery, the above parameters can be adjusted by one skilled in the art of drug delivery to give the desired rate and duration of release.

The amount of injectable solution composition administered will typically depend upon the desired properties of the controlled release implant. For example, the amount of injectable solution composition can influence the length of time in which the biologically active compound is released from the controlled release implant.

According to another aspect of the invention, compositions in the forms of microspheres are produced by encapsulating biologically active compound/polyanion complex in polymeric carrier. The biologically active compound/polyanion complex can be encapsulated using various biocompatible and/or biodegradable polymers having unique properties which are suitable for delivery to different biological environments or for effecting specific functions. The rate of dissolution and, therefore, delivery of biologically active compound is determined by the particular encapsulation technique, polymer composition, polymer crosslinking, polymer thickness, polymer solubility, size and solubility of biologically active compound/polyanion complex.

Biologically active compound/polyanion complex to be encapsulated are suspended in a polymer solution in an organic solvent. The polymer solution must be concentrated enough to completely coat the biologically active compound/polyanion complex after they are added to the solution. Such an amount is one which provides a weight ratio of biologically active compound/polyanion complex to polymer between about 0.01 and about 50, preferably between about 0.1 and about 30. The biologically active compound/polyanion complex should be kept suspended and not allowed to aggregate as they are coated by contact with the polymer.

Preferably, the complex should have a very low solubility in organic solvent used. The reactive groups of the biologically active compound will be bound to the polyanion and thus are not available for interaction with polymer or solvent. This greatly reduces the risk of unfavorable interaction with the polymer.

A polymer solution of the biologically active compound/polyanion complex can therefore be subjected to a variety of microencapsulation techniques including spray drying, spray congealing, emulsion, solvent evaporation emulsion.

According to one embodiment of the invention, the biologically active compound/polyanion complex is suspended in a polymer solution in an organic solvent. The suspended complexes or microparticles along with the polymer and organic solvent are transferred to a larger volume of an aqueous solution containing an emulsifier. In the aqueous solution, the suspended complexes are immersed in the aqueous phase, where the organic solvent evaporates or diffuses away from the polymer. The solidified polymer encapsulates the biologically active compound/polyanion complex to form a composition. The emulsifier helps to reduce the interfacial surface tension between the various phases of matter in the system during the hardening phase of the process. Alternatively, if the encapsulating polymer has some inherent surface activity, there may be no need for addition of a separate surface active agent.

Emulsifiers useful to prepare encapsulated biologically active compound/polyanion complex according to this invention include poloxamers and polyvinyl alcohol as exemplified herein, surfactants and other surface active compounds which can reduce the surface tension between the polymer encapsulated biologically active compound/polyanion complex and the solution.

Organic solvents useful to prepare the microspheres of the present invention include acetic acid, acetone, methylene chloride, ethyl acetate, chloroform and other non-toxic solvents which will depend on the properties of the polymer. Solvents should be chosen that solubilize the polymer and are ultimately non-toxic.

A preferred embodiment of this invention is that the integrity of the biologically active compound/polyanion complex is maintained during the encapsulation process. The complexation is maintained during the suspending process by using an organic solvent in which the biologically active compound/polyanion complex has a very low solubility. Subsequently, once the coated complexes are transferred to the aqueous solvent, rapid hardening of the polymeric carrier and sufficient encapsulation of the biologically active compound/polyanion complex in the previous step shields the complex material from dissolution.

The polymers used to encapsulate the biologically active compound/polyanion complex can be either homo-polymers or co-polymers as described above.

In another embodiment, double-walled polymer coated microspheres may be advantageous. Double-walled polymer coated microspheres may be produced by preparing two separate polymer solutions in methylene chloride or other solvent which can dissolve the polymers. [See Pekarek, K. J.; Jacob, J. S. and Mathiowitz, E. *Double-walled polymer microspheres for controlled drug release, Nature,* 1994, 367, 258-260]. The biologically active compound/polyanion complex are added to one of the solutions and dispersed. Here, the biologically active compound/polyanion complex become coated with the first polymer. Then, the solution containing the first polymer coated biologically active compound/polyanion complex is combined with the second polymer solution. Now, the second polymer encapsulates the first polymer which is encapsulating the biologically active compound/polyanion complex. Ideally, this solution is then dripped into a larger volume of an aqueous solution containing a surface active agent or emulsifier. In the aqueous solution, the solvent evaporates from the two polymer solutions and the polymers are precipitated to encapsulate the complex.

Although the formulations described above are primarily those for injectable or implantable routes of administration, the biologically active compound/polyanion complex of the invention may also be used in the manufacture of orally, nasally, or topically administrable formulations.

Thus, according to the present invention, the compositions containing the biologically active compound/polyanion complex can be administered to a subject where sustained controlled release delivery of a biologically active compound is desired. As used herein, the term "subject" is intended to include warm-blooded animals, preferably mammals, most preferably humans.

As used herein, the term "administered to a subject" is intended to refer to dispensing, delivering or applying a composition (e.g., pharmaceutical formulation) to a subject by any suitable route for delivery of the composition to the desired location in the subject, including delivery by oral, by nasal, by injection and/or implantation subcutaneously, intramuscularly, intraperitoneally, intradermally, intravenously, intraarterially, or intrathecally, by administration to mucosal membranes, or by in situ delivery to provide the desired dosage of a biologically active compound based on the known parameters for treatment of the various medical conditions with the biologically active compound.

The term "controlled release delivery", as defined herein, is intended to refer to continual delivery of a pharmaceutical agent in vivo over a period of time following administration, preferably at least several days to weeks or months. Sustained controlled release delivery of the agent can be demonstrated by, for example, the continued therapeutic effect of the agent over time (e.g., for GLP-1, sustained delivery of the peptide can be demonstrated by continued A1c reductions over time). Alternatively, sustained delivery of the agent may be demonstrated by detecting the presence of the agent in vivo over time.

All books, articles and patents referenced herein are fully incorporated by reference.

EXAMPLES

The following examples illustrate the compositions and methods of the present invention. The following examples should not be considered as limitations, but should merely teach how to make the useful drug delivery systems.

Example 1

Preparation of Doxorubicin Phytate (DOX-PA)

2 mg/mL solution of doxorubicin hydrochloride (MW 578.98) in water (3.45 mM) and 20 mg/mL phytic acid dipotassium salt (MW 736.22) in water (27.2 mM) were prepared. To 100 mL of doxorubicin hydrochloride solution, 2.1 mL of phytic acid solution was added while stirring the solution. The expected ratio of phytic acid to doxorubicin was 1:6. The mixture was centrifuged. The precipitate was washed four times with water and then lyophilized. The yield is 187 mg (88.5%).

The solubility of doxorubicin phytate was measured in deionized water, phosphate buffered saline (PBS, pH 7.4), Dimethylsulfoxide (DMSO), Dimethylacetamide (DMAC), N-Methyl-2-pyrrolidone (NMP), and methoxypolyethylene glycohol 350 (mPEG). Results are shown in the table below:

| Solvents | Solubility (µg/mL) |
|---|---|
| $H_2O$ | 4.5 |
| PBS (pH 7.4) | 11.2 |
| DMSO | Soluble |
| DMAC | 50 |
| NMP | 50 |
| mPEG | 0 |

Example 2

Preparation of Microspheres Containing DOX-PA and DOX-HCl 121 mg DOX-PA complex was dispersed in the solution of PLGA (DL5050 3A, Alkermes) in methylene chloride (DCM). The above organic phase was emulsified in 500 mL of 1.0% (w/v) PVA solution which was pre-cooled in the refrigerator (~4° C.). The emulsion was continued to stir for 3 h at RT to evaporate the DCM. The hardened microspheres were collected by decanting off the supernatant, washed three times with deionized water, and then freeze-dried. Reddish microspheres were obtained. The drug content in the microspheres is ~5.1% as determined by HPLC.

The microspheres containing DOX-HCl were prepared by using DOX-HCl in the place of DOX-PA using the same procedure above.

Example 3

Preparation of Encapsulated Doxorubicin Phytate

The doxorubicin phytate prepared in Example 1 is encapsulated in polylactic-co-glycolic acid (PLGA) using a double emulsion method. 1.4 mg of doxorubicin phytate is added in methylene chloride containing PLGA (0.6 g PLGA/ml solvent; 20 ml). The mixture is homogenized for 30 sec at 3,000 rpm, using a homogenizer with a microfine tip. The resulting suspension is transferred to a stirred tank (2000 ml) containing 1% poly(vinyl alcohol) (PVA) and methylene chloride (4.5 ml). The solution is mixed at 1,000 rpm for 1 min. The microspheres in the PVA solution are precipitated by immersion in distilled water, washed and filtered. The microspheres are then washed with distilled water containing 0.1% Tween, to reduce agglomeration and dried with nitrogen for 2 days at 4° C.

Example 4

Preparation of Tetracaine Phytate 1.0 g tetracaine hydrochloride (3.33 mmol) was dissolved in 40 mL water and with vigorous stirring, 20.5 mL of the phytic acid solution of Example 1 was added. After another 30 min of stirring, the precipitate was centrifuged and washed with water. The final products were in the form of white powder. The solubility of the complex in different buffers is shown below.

| Solvents | Solubility (mg/mL) |
|---|---|
| PBS (pH 7.4) | 7.5 |
| $H_2O$ (~pH 6.0) | 4.5 |
| Acetate Buffer (pH 4.5) | 2.7 |

Example 5

Preparation of Polymer Microspheres Containing Tetracaine

Polymer (e.g., poly(lactide-co-glycolide) (PLGA) microspheres were prepared by an oil-in-water (O/W) single emulsion technique. PLGA was dissolved in methylene chloride (DCM). For the encapsulation of tetracaine, the drug was mixed with the PLGA solution in DCM. The mixed solution or suspension was emulsified in 500 mL of 0.5-1% (w/v) PVA (PVA, 88% hydrolyzed, average molecular weight of 31,000-50,000, Sigma-Aldrich) solution pre-cooled in the refrigerator at 4° C. The emulsion was stirred continuously for 3 h at RT to evaporate the DCM. The hardened microspheres were collected, washed three times with deionized water, and then freeze-dried.

In the case of preparation of microspheres containing tetracaine phytate (TCPA), 210 mg of TCPA was suspended in 5 mL PLGA solution. The suspension was sonicated for 10 min. This suspension was slowly added to the continuous phase (1% PVA solution) pre-cooled at 4° C. while stirring. The emulsion was stirred continuously for 3 h at room temperature to evaporate the DCM. The hardened microspheres were collected, washed three times with deionized water, and then freeze-dried. The tetracaine load was about 3.2%.

Polymer microspheres containing tetracaine hydrochloride (TC-HCl) were prepared in a similar manner by replacing TCPA with TC-HCl.

Example 6

Preparation of Pellets Containing Tetracaine Phytate

Implantable pellets containing tetracaine phytate was prepared by compression molding process. 249 mg PLGA powder were thoroughly mixed with 25.7 mg tetracaine phytate using a mortar and pestle. Then ~50 mg mixture were molded using a Delta Press to form a pellet. The pellets containing tetracaine hydrochloride were also prepared for comparison.

Example 7

Preparation of Implants Containing Tetracaine Phytate 2.56 g of poly(lactide-co-glycolide) (PLGA) (RG504H, from Boehringer-Ingelheim) is dissolved in 7.73 grams of methylene chloride. To this solution, 256 mg of tetracaine phytate is added and dispersed with a high shear mixer.

The resulting mixture is placed in a rotating evaporator and the majority of the methylene chloride is removed under vacuum. The resulting thick dispersion is poured onto a glass plate and spread with an adjustable blade set at 0.7 mm.

The film thus obtained is melted and compression molded at 80° C. to give a film about 0.5 mm thick. The film is incubated in phosphate buffered saline (containing 0.02% sodium azide) at pH 7.4 and 37° C., and the buffer solution is assayed periodically by UV to determine the amount of tetracaine released.

Similar molded implants can be manufactured using, in place of tetracaine, other biologically active compound containing at least one basic functional group.

Example 8

Injectable Formulations of Tetracaine Phytate and its In Vitro Release

40% (w/v) of poly(DL-lactide-co-glycolide) (PLGA) having a carboxy terminal group solution in NMP is prepared by dissolving 160 mg of PLGA (RG503H, from Boehringer-Ingelheim) in 0.4 mL NMP. 39.9 mg of tetracaine phytate is mixed with the polymer solution by syringe flushing. Small drops of the mixture (about 100 mg) are added to phosphate buffered saline solution at pH 7.4. The receiving fluid is replaced at selected time points with fresh solution, and the removed PBS solution is analyzed for drug concentration using UV detection at 280 nm.

Example 9

Preparation of the Complex of Lidocaine with Phytic Acid 1.0 g lidocaine hydrochloride (3.69 mmol) is dissolved in 400 mL water and with vigorous stirring, 28.8 mL of the phytate solution of Example 1 is added. After 30 min, the pH is adjusted to 3.5 with 0.1 N HCl solution. After another 30 min of stirring, the precipitate is filtered and washed 4 times with water. The final product is lyophilized.

Example 10

Preparation of the Complex of Amoxicillin with Phytic Acid 1.0 g amoxicillin hydrochloride (2.74 mmol) is dissolved in 400 mL water and with vigorous stirring, 21.3 mL of the phytate solution of Example 1 is added. After 30 min, the pH is adjusted to 3.5 with 0.1 N HCl solution. After another 30 min of stirring, the precipitate is filtered and washed 4 times with water. The final product is lyophilized.

Similar complexes may be manufactured by using, in place of amoxicillin hydrochloride, other compounds containing at least one basic group.

Example 11

Preparation of the Complex of Octreotide with Phytic Acid 20 mg/mL solution of octreotide was prepared by dissolving 215 mg octreotide in 10.75 mL water. 5 mL of this solution was mixed with 1.45 ml of PA solution (1%, w/v) at pH 3.12. The mixture was vortexed for 1 min and then the mixture was put on a rotator to mix for another hour. The complex was separated by centrifugation and rinsed with water once. The precipitated product was freeze dried for 48 h. The final product in the form of white powder was obtained.

Example 12

The Stability of Octreotide in Injectable Formulations

Injectable formulations of octreotide were prepared by dispersing octreotide in polymer solution in an appropriate solvent. For example, poly(DL-lactide-co-glycolide) (PLGA) having a 50/50 ratio of lactide to glycolide (PLG DL2.5A from Alkermes) was dissolved in N-methyl-2-pyrrolidone (NMP), or methoxypolyethylene glycol (mPEG), or polyethylene glycol dimethyl ether (PEGDM) to give a 40% solution by weight. The injectable formulations were prepared by dispersing octreotide phytate or acetate in the polymer solutions. The mixture was thoroughly mixed until a uniform suspension or solution was obtained. Six injectable formulations were prepared as shown below.

| Polymer Solutions | Targeted Loading | Salt Form | Drug (mg) | PLGA/Sol. (mg) |
|---|---|---|---|---|
| 40% 5050DL2.5A/60% NMP | 50 mg/ml | Acetate | 20 | 455 |
| 40% 5050DL2.5A/60% NMP | 50 mg/ml | Phytate | 20 | 445 |
| 40% 5050DL2.5A/60% mPEG | 50 mg/ml | Acetate | 20 | 450 |
| 40% 5050DL2.5A/60% mPEG | 50 mg/ml | Phytate | 20 | 430 |
| 40% 5050DL2.5A/60% PEGDM | 50 mg/ml | Acetate | 20 | 445 |
| 40% 5050DL2.5A/60% PEGDM | 50 mg/ml | Phytate | 20 | 440 |

Note:
mPEG: Methoxy polyethyleneglycol 350;
NMP: N-methyl Pyrrolidinone;
PEGDM: polyethylene glycohol dimethyl ether The stability of octreotide in the above injectable formulations at room temperature was monitored by HPLC and the results are shown in the table below. The complexation of octreotide with phytic acid completely prevented the degradation and/or acylation of octreotide in PLGA solutions in mPEG and PEGDM, while a slight degradation of octreotide was observed in PLGA solutions in NMP at room temperature over time. When octreotide acetate was used, significant amount of the octreotide was degraded or reacted after three days at room temperature. In the case of PLGA solution in NMP, almost 100% of octreotide was degraded or acylated. Therefore, octreotide phytate would be the preferred form to prepare stable formulations containing the peptide.

| | % of intact octreotide | | | | | |
|---|---|---|---|---|---|---|
| Time (h) | NMP/Ac | NMP/Pa | mPEG/Ac | mPEG/Pa | PEGDM/Ac | PEGDM/Pa |
| 0 | 100.0 | 100.0 | 100.0 | 100.0 | 100.0 | 100.0 |
| 0.5 | 95.5 | 100.0 | 100.0 | 100.0 | 100.0 | 100.0 |
| 1 | 92.4 | 100.0 | 100.0 | 100.0 | 100.0 | 100.0 |
| 3 | 90.0 | 99.0 | 100.0 | 100.0 | 100.0 | 100.0 |
| 5 | 58.0 | 100.0 | 100.0 | 100.0 | 95.0 | 100.0 |
| 24 | 15.4 | 100.0 | 100.0 | 100.0 | 100.0 | 100.0 |
| 72 | 0.8 | 80.4 | 40.2 | 100.0 | 69.9 | 100.0 |
| 120 | 0.0 | 81.5 | 64.0 | 100.0 | 32.7 | 100.0 |
| 168 | 0.0 | 85.0 | 32.5 | 100.0 | 58.8 | 100.0 |
| 288 | 0.0 | 81.1 | 53.9 | 100.0 | 24.4 | 100.0 |

Note:
mPEG: Methoxy polyethyleneglycol 350;
NMP: N-methyl Pyrrolidinone;
PEGDM: polyethylene glycohol dimethyl ether;
/Ac: Octreotide in acetate form;
/Pa: Octreotide in phytate form.

Example 13

The Stability of Octreotide in Injectable Formulations

Poly(DL-lactide-co-glycolide) (PLGA) having a 50/50 ratio of lactide to glycolide (DL2.5A from Alkermes) was dissolved in N-methyl-2-pyrrolidone (NMP), or methoxy-polyethylene glycohol (mPEG) to give a 40% solution by weight. The injectable polymer solutions were prepared by dispersing octreotide phytate or acetate or citrate. The mixture was thoroughly mixed until a uniform suspension or solution was obtained. Injectable formulations were prepared as shown below.

| Formulation | Targeted Loading | Salt Form | Drug (mg) | PLGA/Sol (mg) |
|---|---|---|---|---|
| 40% 5050DL2.5A/60% NMP | 50 mg/ml | Phytate | 20 | 445 |
| 40% 5050DL2.5A/60% NMP | 50 mg/ml | Acetate | 20 | 455 |
| 40% 5050DL2.5A/60% NMP | 50 mg/ml | Citrate | 24 | 455 |
| 40% 5050DL2.5A/60% PEG350 | 50 mg/ml | Phytate | 20 | 450 |

Note:
mPEG: Methoxy polyethyleneglycol 350;
NMP: N-methyl Pyrrolidinone.

The stability of octreotide in the above injectable formulations at room temperature was monitored by HPLC and the results are shown in the table below. It appears that both salt forms of octreotide and the solvent affect the stability of octreotide. In terms of the stability of octreotide, mPEG is preferred than NMP and phytate complex form of octreotide is preferred than acetate and citrate salt of octreotide.

| | % of intact octreotide | | | |
|---|---|---|---|---|
| Time points (h) | NMP/Ac | mPEG/Ac | NMP/Ca | mPEG/Pa |
| 0 | 100.0 | 100.0 | 100.0 | 100.0 |
| 1 | 79.8 | 100.0 | 94.9 | 100.0 |
| 5 | 43.7 | 100.0 | 57.7 | |
| 24 | 16.1 | 82.2 | 41.5 | 100.0 |
| 72 | 0.0 | 68.2 | 24.8 | |
| 168 | 0.0 | 54.5 | 13.5 | 100.0 |
| 336 | 0.0 | 37.4 | 0.0 | 100.0 |
| 504 | 0.0 | 28.5 | 0.0 | 100.0 |

Note:
mPEG: Methoxy polyethyleneglycol 350;
NMP: N-methyl Pyrrolidinone;
/Ac: Octreotide in acetate form;
/Ca: Octreotide in citrate form;
/Pa: Octreotide in phytate form.

Example 14

Release of Octreotide In Vivo in Rats

Poly(DL-lactide-co-glycolide) (PLGA) was dissolved in N-methyl-2-pyrrolidone (NMP), or methoxypolyethylene glycohol (mPEG) to give a 40% solution by weight. The injectable formulations were prepared by dispersing octreotide phytate or acetate. The mixture was thoroughly mixed until a uniform suspension or solution was obtained. Injectable formulations prepared are shown in the table below. These formulations of octreotide (roughly about 100 uL) were administered subcutaneously in the back of the Sprague-Dawley male rats. The release of octreotide was determined by implant retrieval at predefined time intervals (30 min for group G and 24 h for groups A through F) after ministration and analysis of the octreotide remaining in the implant. The stability of octreotide during the formulation and release was also evaluated.

| ID# | Formulation | Drug Content (%) | Harvest Time (h) | Degradation (%) | Mean Release (%) |
|---|---|---|---|---|---|
| A | OCT/Pa in 40% 5050 DL2.5A/60% mPEG | 4.36 | 24 | 0.00 | 10.82 ± 7.10 |
| B | OCT/Ac in 40% 5050 DL2.5A/60% mPEG | 4.16 | 24 | 20.60 ± 1.53 | 47.01 ± 6.91 (34.47 ± 8.51)* |
| C | OCT/Pa in 40% 5050 DL3A/60% mPEG | 4.37 | 24 | 0.00 | 62.08 ± 10.94 |
| D | OCT/Pa in 40% 5050 DL3A/60% NMP | 4.36 | 24 | 12.67 ± 2.52 | 75.52 ± 3.06 |
| E | OCT/Pa 40% 5050 DL2.5A/60% NMP | 4.35 | 24 | 10.00 | 63.41 ± 5.97 |
| F | OCT/Ac in 40% 5050 DL2.5A/60% NMP | 4.26 | 24 | 28.81 ± 3.45 | 28.82 ± 5.02 (44.12 ± 3.94)* |
| G | OCT/Pa in 40% 5050 DL2.5A/60% mPEG | 4.60 | 0.5 | 0.00 | 3.29 ± 7.73 |

Note:
mPEG: Methoxy polyethyleneglycol 350;
NMP: N-methyl Pyrrolidinone;
OCT: Octreotide;
OCT/Ac: Octreotide actate;
OCT/Pa: Octreotide phytate.
*Including degradation peaks Formulations A and G are similar with a slight higher drug content for G, but the animals were harvested and implants were retrieved at different time points. The results appear to show the gradual release of octreotide over time. The octreotide released from the implants was about 3.29±7.73% in group G at 0.5 hour and 10.82±7.10% in group A at 24 hours post administration. Comparing to formulation B, the complexation of octreotide with phytic acid significantly improved both initial release and stability of the peptide in the formulation and release processes. The results also showed that mPEG was a preferred solvent over NMP in terms of octreotide stability. NMP seems to be a better solvent for both octreotide and PLGA which may promote the acylation reaction between octreotide and PLGA or its degradation products.

The results on octreotide stability in PLGA/NMP vehicle correlate to those obtained in vitro (refer to example 13 & 14). However, the degradation/reaction rate seemed slower in vivo than that in vitro (30% vs 85% after 24 h). This difference could be explained by the fact that the implant was quickly formed after administration by dissipating solvent NMP to the surrounding tissues of the animals. The solvent dissipation would result in the increase of viscosity of the vehicle or solidification of the PLGA, leading to a slower reaction rate between octreotide and PLGA or its degradation products. However, the solvent dissipation was a slow process as significant amount of NMP (up to 35%) could still be detected in the implant 24 hours after administration. This indicates that the residual solvent may be trapped in the implant much longer than desired. Therefore, the use of biologically active compound in its more stable form is very important to develop a beneficial formulation.

Example 15

In Vivo Release of Octreotide in Rats

The injectable formulations were prepared by dispersing octreotide phytate in Poly(DL-lactide-co-glycolide) (PLGA) solution in mPEG350. The mixture was thoroughly mixed until a uniform suspension was obtained. Injectable formulations prepared are shown in the table below. These formulations of octreotide (roughly about 100 uL) were administered subcutaneously in the back of the Sprague-Dawley male rats. The release of octreotide was determined by implant retrieval at predefined time intervals after administration and analysis of the octreotide remaining in the implant. The stability of octreotide during the formulation and release was also evaluated.

| ID# | Formulation | Drug Content (%) | Harvest Time (h) | Mean Release (%) | Standard Deviation (%) |
|---|---|---|---|---|---|
| A | OCT/Pa in 40% 5050 DL2.5A/60% mPEG | 3.9 | 24 | 11.1 | 1.7 |
| B | OCT/Ac in 35% 5050 DL2.5A/65% mPEG | 3.9 | 24 | 14.0 | 4.2 |
| C | OCT/Pa in 50% RG752S/50% mPEG | 10.8 | 24 | 0.4 | 2.0 |
| D | OCT/Pa in 45% RG752S/55% mPEG | 10.7 | 24 | 1.5 | 2.7 |
| E | OCT/Pa 40% RG752S/60% mPEG | 10.8 | 24 | 3.8 | 4.5 |

Note:
mPEG: Methoxy polyethyleneglycol 350;
NMP: OCT: Octreotide;
OCT/Pa: Octreotide phytate.
5050DL2.5A: poly(lactide-co-glycolide) with 50% lactide from Alkermes;
RG752S: poly(lactide-co-glycolide) with 75% lactide from Boehringer-Ingelheim (BI).

The initial release of OCT from formulations A and B were 11.1±1.7% and 14.0±4.2% respectively, while from formulations C, D, and E were 0.4±2.0%, 1.5±2.7%, and 3.8±4.5% respectively. Although the difference was not statistically significant, there seems a tendency that the initial release of OCT increases with the decrease of polymer concentration. In addition, OCT was stable during the formulation process and in vivo release in these formulations.

Example 16

Preparation of the Complex of Glycagon Like Peptide 1 (GLP-1) with Phytic Acid 50 mg GLP-1 acetate (Mw 3297.7, 0.0152 mmol) was dissolved in 5 mL water and with vigorous stirring, 1.01 mL of 1% phytic acid solution at pH 3.2 was added (a molar ratio of GLP-1:phytate=1:1). After another 30 min of stirring, the mixture was centrifuged. The supernatant was decanted off and the precipitate was rinsed twice with water and then freezedried. The final product was in the form of white powder.

Example 17

Preparation of the Complex of Glycagon Like Peptide 1 (GLP-1) with Inositol Hexasulfate (InS6)

50 mg GLP-1 acetate (Mw 3297.7, 0.0152 mmol) was dissolved in 5 mL water and with vigorous stirring, 1.35 mL of 1% potassium inositol hexasulfate (InS6) solution at pH 1.0 was added (a molar ratio of GLP-1:InS6=1:1). After another 30 min of stirring, the mixture was centrifuged. The supernatant was decanted off and the precipitate was rinsed twice with water and then freeze-dried. The final product was in the form of white powder.

Example 18

Preparation of the Complex of PYY with Phytic Acid 1.0 g PYY acetate (0.247 mmol) is dissolved in 100 mL water and with vigorous stirring, 11.5 mL of the phytate solution of Example 1 is added (a molar ratio of PYY:phytate=1:1). After another 30 min of stirring, the precipitate is filtered and washed 4 times with water. The final product is lyophilized.

Example 19

Preparation of Lysozyme Phytate 100 mg lysozyme (7.1 ☐mol) was dissolved in 40 mL water and with vigorous stirring, 3.1 ☐L of the phytate solution of Example 1 was added. After another 30 min of stirring, the precipitate was filtered, washed 4 times with water, and lyophilized. The final product in the form of white powder was obtained.

Similar complexes may be manufactured by using, in place of lysozyme, either naturally occurring peptides/proteins or their synthetic analogues.

We claim:
1. A pharmaceutical composition comprising:
a) an ionic complex that is formed between i) a biologically active compound having at least one basic, positively charged functional group and ii) a polyanion that is inositol hexaphosphate or inositol hexasulphate; and
b) a pharmaceutically acceptable carrier comprising a biodegradable, water-insoluble polymer.
2. The pharmaceutical composition of claim 1 wherein the inositol is selected from the group consisting of cis-inositol, epi-inositol, allo-inositol, neo-inositol, myo-inositol, muco-inositol, scyllo-inositol, L-(−)-chiro-inositol, and D-(+)-chiro-inositol.
3. The pharmaceutical composition of claim 1 wherein the inositol is myo-inositol.
4. The pharmaceutical composition of claim 1 wherein the polyanion is inositol hexaphosphate.
5. The pharmaceutical composition of claim 1 wherein the polyanion is inositol hexasulphate.
6. The pharmaceutical composition of claim 1 wherein the biologically active compound has at least one basic nitrogen.
7. The pharmaceutical composition of claim 6 wherein the basic nitrogen is selected from the group consisting of amine, imine and ring nitrogen.
8. The pharmaceutical composition of claim 1 wherein the biologically active compound is selected from the group consisting of small molecules, macromolecules, peptides, proteins, and enzymes.
9. The pharmaceutical composition of claim 1 wherein the biologically active compound is selected from the group consisting of doxorubicin, diltiazem, cyclobenzaprine, noscapine, nortriptyline, quinidine, ergotamine, benztropine, verapamil, flunarizine, imipramine, pyrimethamine, naltrexone, lidocaine, prilocaine, mepivacaine, bupivacaine, tetracaine, ropivacaine, oxytocin, vasopressin, adrenocorticotropic hormone (ACTH), epidermal growth factor (EGF), platelet-derived growth factor (PDGF), prolactin, luteinising hormone, luteinizing hormone releasing hormone (LHRH), LHRH agonists, LHRH antagonists, growth hormones (including human, porcine, and bovine), growth hormone releasing factor, insulin, erythropoietin (including all proteins with erythropoietic activity), somatostatin, glucagon, interleukin, interferon-.alpha., interferon-.beta., interferon-.gamma., gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), exenatide, peptide YY (PYY), renin, bradykinin, bacitracins, polymyxins, colistins, tyrocidine, gramicidins, cyclosporins (which includes synthetic analogues and pharmacologically active fragments thereof), enzymes, cytokines, vaccines, antibiotics, antibodies, glycoproteins, follicle stimulating hormone, kyotorphin, taftsin, thymopoietin, thymosin, thymostimulin, thymic humoral factor, serum thymic factor, colony stimulating factors, motilin, bombesin, dinorphin, neurotensin, cerulein, urokinase, kallikrein, substance P analogues and antagonists, angiotensin II, blood coagulation factor VII and IX, lysozyme, gramicidines, melanocyte stimulating hormone, thyroid hormone releasing hormone, thyroid stimulating hormone, pancreozymin, cholecystokinin, human placental lactogen, human chorionic gonadotrophin, protein synthesis stimulating peptide, gastric inhibitory peptide, vasoactive intestinal peptide, and platelet derived growth factor.
10. The pharmaceutical composition of claim 8 wherein the biologically active compound is selected from the group consisting of doxorubicin, rapamycin, naltrexone, epidermal growth factor (EGF), LHRH agonists, LHRH antagonists, growth hormones, growth hormone releasing factor, octreotide, interferon-alpha, interferon-beta, interferon-gamma, calcitonin, parathyroid hormone (PTH), glucagon-like peptide (GLP-1), and peptide YY (PYY).
11. The pharmaceutical composition of claim 1 wherein the biologically active compound is doxorubicin.
12. The pharmaceutical composition of claim 1 wherein the biologically active compound is glycagon like peptide 1 (GLP-1) and its analogues.
13. The pharmaceutical composition of claim 1 wherein the biologically active compound is Octreotide.
14. The pharmaceutical composition of claim 1 wherein the biologically active compound is peptide YY (PYY).
15. The pharmaceutical composition of claim 1 wherein the biodegradable, water insoluble polymer is selected from the group consisting of polylactides, polyglycolides, poly

(lactide-co-glycolide)s, polycaprolactones, polydioxanones, polycarbonates, polyhydroxybutyrates, polyalkylene oxalates, polyanhydrides, polyamides, polyesteramides, polyurethanes, polyacetals, polyorthocarbonates, polyphosphazenes, polyhydroxyvalerates, polyalkylene succinates, polyorthoesters, and copolymers, block copolymers, branched copolymers, terpolymers and combinations and mixtures thereof.

16. The pharmaceutical composition of claim 1 wherein the pharmaceutically acceptable carrier comprises an environment responsive polymer or gel.

17. The pharmaceutical composition of claim 16 wherein the environment responsive polymer or gel is thermosensitive, pH sensitive, or electrically sensitive.

18. The pharmaceutical composition of claim 1 in the form selected from the group consisting of injectable solutions or suspensions, particles, films, pellets, cylinders, discs, microcapsules, microspheres, nanospheres, microparticles, wafers, micelles, and liposomes.

19. The pharmaceutical composition of claim 9 wherein the antibiotic is selected from the group consisting of doxycyclin, bacitracin, erythromycin, polymyxin, vancomycin, gentamycin, kanamycin, neomycin, amoxicillin, amikacin, arbekacin, bambermycins, butirosin, dibekacin, dihydrostreptomycin, fortimicin, isepamicin, micronimicin, netilmicin, paromycin, ribostamycin, rapamycin, sisomicin, streptomycin and tobramycin.

* * * * *